United States Patent
Kurnik et al.

(10) Patent No.: US 8,219,324 B2
(45) Date of Patent: Jul. 10, 2012

(54) REAL-TIME PCR ELBOW CALLING BY EQUATION-LESS ALGORITHM

(75) Inventors: Ronald T. Kurnik, Foster City, CA (US); Martin Titz, Rotkreuz (CH)

(73) Assignee: Roche Molecular Systems, Inc., Pleasanton, CA (US)

( * ) Notice: Subject to any disclaimer, the term of this patent is extended or adjusted under 35 U.S.C. 154(b) by 867 days.

(21) Appl. No.: 12/209,912

(22) Filed: Sep. 12, 2008

(65) Prior Publication Data

US 2010/0070185 A1    Mar. 18, 2010

(51) Int. Cl.
*G01N 33/48* (2006.01)
(52) U.S. Cl. .......................................................... 702/19
(58) Field of Classification Search ...................... 702/19
See application file for complete search history.

(56) References Cited

U.S. PATENT DOCUMENTS

| | | |
|---|---|---|
| 6,303,305 B1 | 10/2001 | Wittwer et al. |
| 6,503,720 B2 | 1/2003 | Wittwer et al. |
| 6,783,934 B1 | 8/2004 | McMillan et al. |
| 7,179,589 B2 | 2/2007 | Brookes |
| 7,228,237 B2 | 6/2007 | Woo et al. |

*Primary Examiner* — Jerry Lin
(74) *Attorney, Agent, or Firm* — Kilpatrick Townsend & Stockton LLP

(57) ABSTRACT

Systems and methods for determining a transition value in a sigmoid or growth curve, such as the end of the baseline region or the elbow value or Ct value of a PCR amplification curve. Numerical determinations of the second derivatives and curvature values of a PCR data set are made. A Gaussian Mixture Model (GMM) function with parameters determined using a Levenberg-Marquardt (LM), or other, regression process is used to find an approximation to the second derivative values and to the curvature values, where the maximum values of the numerically determined second derivative values and/or curvature values are used as initial conditions for parameters of the GMM function. The determined parameters provide fractional Ct values. The Ct value(s) are then returned and may be displayed or otherwise used for further processing.

32 Claims, 10 Drawing Sheets

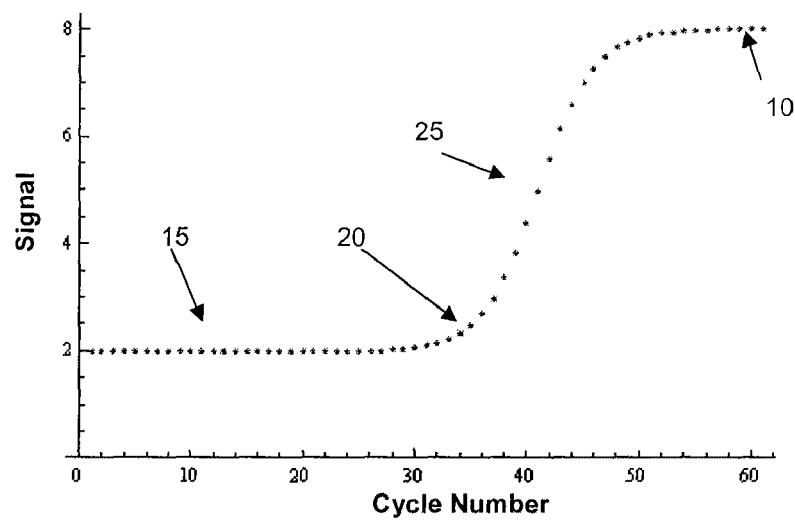
Figure 1: Real-Time PCR Curve
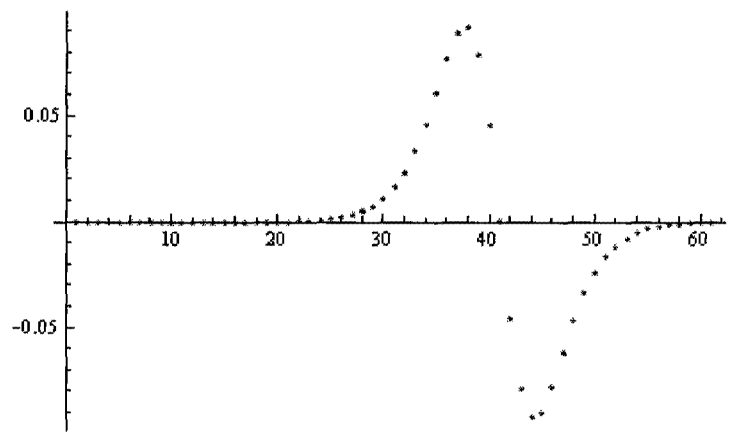
Figure 2: Second Derivative of Real-Time PCR Curve in Figure 1
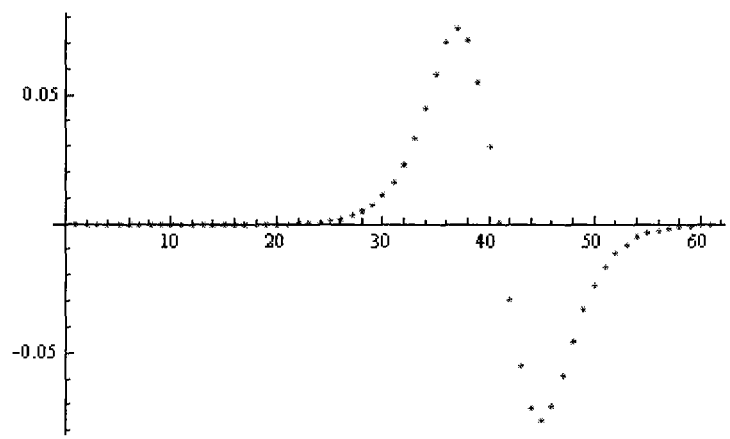
Figure 3: Curvature of Real-Time PCR Curve in Figure 1

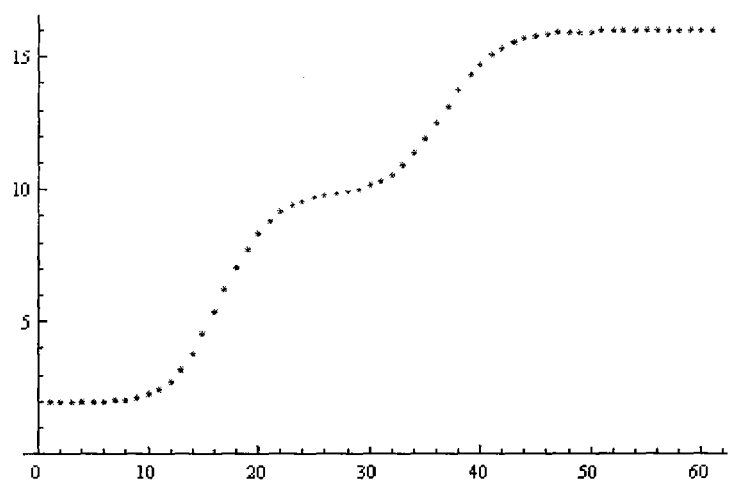
Figure 5: Real-Time PCR Curve with Multiple Ct values
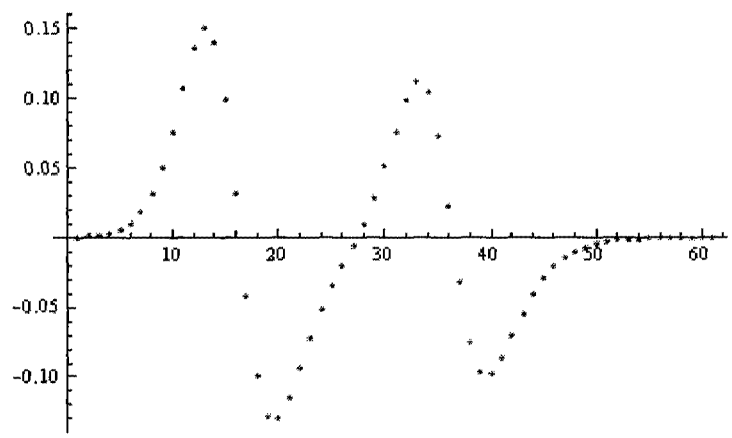
Figure 6: Second Derivative Corresponding to Figure 4
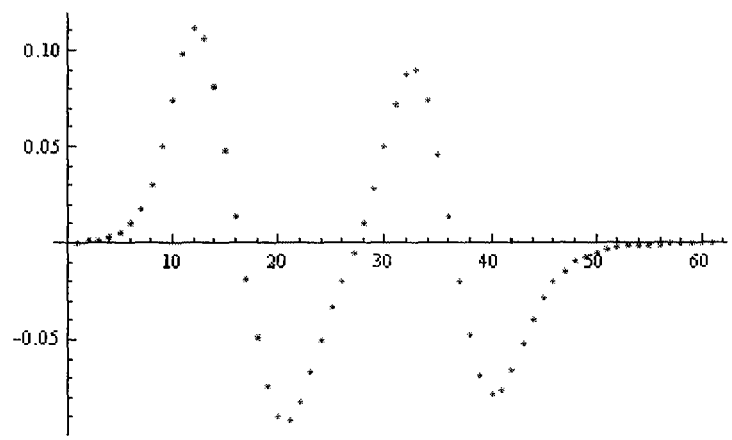
Figure 7: Curvature Corresponding to Figure 4

Figure 9: Decline Detection Workflow

Figure 10: Distinguishing Growth from Straight Line

Figure 12: Ct Finding Routine

Figure 13: Expert System

REAL-TIME PCR ELBOW CALLING BY EQUATION-LESS ALGORITHM

BACKGROUND

The present invention relates generally to systems and methods for processing data representing sigmoid or growth curves, and more particularly to systems and methods for determining characteristic cycle threshold (Ct) or elbow values in Polymerase Chain Reaction (PCR) amplification curves, or elbow values in other growth curves.

The Polymerase Chain Reaction is an in vitro method for enzymatically synthesizing or amplifying defined nucleic acid sequences. The reaction typically uses two oligonucleotide primers that hybridize to opposite strands and flank a template or target DNA sequence that is to be amplified. Elongation of the primers is catalyzed by a heat-stable DNA polymerase. A repetitive series of cycles involving template denaturation, primer annealing, and extension of the annealed primers by the polymerase results in an exponential accumulation of a specific DNA fragment. Fluorescent probes or markers are typically used in the process to facilitate detection and quantification of the amplification process.

A typical real-time PCR curve is shown in FIG. 1, where fluorescence intensity values are plotted vs. cycle number for a typical PCR process. In this case, the formation of PCR products is monitored in each cycle of the PCR process. The amplification is usually measured in thermocyclers which include components and devices for measuring fluorescence signals during the amplification reaction. An example of such a thermocycler is the Roche Diagnostics LightCycler (Cat. No. 20110468). The amplification products are, for example, detected by means of fluorescent labelled hybridization probes which only emit fluorescence signals when they are bound to the target nucleic acid or in certain cases also by means of fluorescent dyes that bind to double-stranded DNA.

For a typical PCR curve, identifying a transition point at the end of the baseline region, which is referred to commonly as the elbow value or cycle threshold (Ct) value, is extremely useful for understanding characteristics of the PCR amplification process. The Ct value may be used as a measure of efficiency of the PCR process. For example, typically a defined signal threshold is determined for all reactions to be analyzed and the number of cycles (Ct) required to reach this threshold value is determined for the target nucleic acid as well as for reference nucleic acids such as a standard or housekeeping gene. The absolute or relative copy numbers of the target molecule can be determined on the basis of the Ct values obtained for the target nucleic acid and the reference nucleic acid (Gibson et al., Genome Research 6:995-1001; Bieche et al., Cancer Research 59:2759-2765, 1999; WO 97/46707; WO 97/46712; WO 97/46714). The elbow value in region 20 at the end of the baseline region 15 in FIG. 1 would be in the region of cycle number 38.

The elbow value in a PCR curve can be determined using several existing methods. For example, various current methods determine the actual value of the elbow as the value where the fluorescence reaches a predetermined level called the AFL (arbitrary fluorescence value). Other methods use equation-based approaches to determining PCR elbows for curves that have typical double sigmoid type shapes. An equation that has proven very useful in describing sigmoid type shapes is the double sigmoid equation. Various implementations and processing of the double sigmoid equation have been introduced, for example the DSLM (double sigmoid Levenberg-Marquardt) equation, the DSLM with options for baseline subtraction (BLS), baseline division (BLD), and baseline subtraction with division (BLSD), the Curvature equation and others as described in U.S. application Ser. No. 11/316,315, filed Dec. 20, 2005; U.S. application Ser. No. 11/349,550, filed Feb. 6, 2006; U.S. application Ser. No. 11/458644, filed Jul. 19, 2006; U.S. application Ser. No. 11/533,291, filed Sep. 19, 2006; and U.S. application Ser. No. 11/861,188, filed Sep. 25, 2007, the disclosures of which are each hereby incorporated by reference for all purposes. If the PCR curve, however, has a geometry that does not fit the typical double sigmoid type shape, then the double sigmoid based methods may no longer be applicable, thus requiring a more generic approach to obtaining elbow or Ct values.

Therefore it is desirable to provide systems and methods for determining the elbow value in growth curves, and PCR curves in particular, which overcome the above and other problems.

BRIEF SUMMARY OF THE INVENTION

The present invention provides systems and methods for determining a transition value in a sigmoid or growth curve, such as the end of the baseline region or the elbow value or Ct value of a PCR amplification curve.

In order to meet the need for a generic, yet robust method to determine PCR elbow values such as Real-Time PCR elbows, various embodiments use positions of maxima from the data (e.g., maxima in the curvature, relative curvature, second derivative, or relative second derivative) to find elbow values. Determination of these values does not require an equation per se, but rather uses numerical methods. Various embodiments, however, use Gaussian Mixture Models, which do require equations to fit the data and in turn determine fractional elbow values.

According to one aspect of the present invention, a computer-implemented method is provided for determining a point at the end of a baseline region of a growth curve. The method typically includes receiving a dataset representing a growth curve, the dataset including a plurality of data points each having a pair of coordinate values, numerically determining second derivative values for data points along the growth curve, and determining a maximum value of the determined second derivative values. The method also typically includes calculating an approximation of a curve that fits the determined second derivative values by applying a regression process to a Gaussian Mixture Model function to determine one or more parameters of the function, wherein the parameters include initial conditions, and wherein the maximum value is used as an initial condition for a first parameter, and outputting the first parameter, wherein the determined first parameter represents the end of the baseline region of the growth curve. In certain aspects, the dataset represents a growth curve for a kinetic Polymerase Chain Reaction (PCR) process, and wherein the point at the end of the baseline region represents an elbow or cycle threshold (Ct) value of the growth curve. In certain aspects, the regression process includes a Levenberg-Marquardt (LM) regression process. In certain aspects, a second maximum value is used as an initial condition for a second parameter, and the method further includes outputting the second parameter.

According to another aspect of the present invention, a computer-implemented method is provided for determining a point at the end of a baseline region of a growth curve. The method typically includes receiving a dataset representing a growth curve, the dataset including a plurality of data points each having a pair of coordinate values, numerically determining curvature values for data points along the growth curve, and determining a maximum value of the determined curvature values. The method also typically includes calculating an approximation of a curve that fits the determined curvature values by applying a regression process to a Gaussian Mixture Model function to determine one or more parameters of the function, wherein the parameters include initial conditions, and wherein the maximum value is used as an initial condition for a first parameter, and outputting the first parameter, wherein the determined first parameter represents the end of the baseline region of the growth curve. In certain aspects, the dataset represents a growth curve for a kinetic Polymerase Chain Reaction (PCR) process, and wherein the point at the end of the baseline region represents an elbow or cycle threshold (Ct) value of the growth curve. In certain aspects, the regression process includes a Levenberg-Marquardt (LM) regression process. In certain aspects, a second maximum value is used as an initial condition for a second parameter, and the method further includes outputting the second parameter.

According to another aspect of the present invention, a computer readable medium is provided that includes code for controlling a processor to determine a point at the end of the baseline region of a growth curve. The code typically includes instructions to receive a dataset representing a growth curve, the dataset including a plurality of data points each having a pair of coordinate values, to numerically determine second derivative values for data points along the growth curve, and to determine a maximum value of the determined second derivative values. The code also typically includes instructions to calculate an approximation of a curve that fits the determined second derivative values by applying a regression process to a Gaussian Mixture Model function to determine one or more parameters of the function, wherein the parameters include initial conditions, and wherein the maximum value is used as an initial condition for a first parameter, and to output the first parameter, wherein the determined first parameter represents the end of the baseline region of the growth curve. In certain aspects, the dataset represents a growth curve for a kinetic Polymerase Chain Reaction (PCR) process, and the point at the end of the baseline region represents an elbow or cycle threshold (Ct) value of the growth curve. In certain aspects, the regression process includes a Levenberg-Marquardt (LM) regression process. In certain aspects, a second maximum value is used as an initial condition for a second parameter, and the code further includes instructions to output the second parameter.

According to another aspect of the present invention, a computer readable medium is provided that includes code for controlling a processor to determine a point at the end of the baseline region of a growth curve. The code typically includes instructions to receive a dataset representing a growth curve, the dataset including a plurality of data points each having a pair of coordinate values, to numerically determine curvature values for data points along the growth curve, and to determine a maximum value of the determined curvature values. The code also typically includes instructions to calculate an approximation of a curve that fits the determined curvature values by applying a regression process to a Gaussian Mixture Model function to determine one or more parameters of the function, wherein the parameters include initial conditions, and wherein the maximum value is used as an initial condition for a first parameter, and to output the first parameter, wherein the determined first parameter represents the end of the baseline region of the growth curve. In certain aspects, the dataset represents a growth curve for a kinetic Polymerase Chain Reaction (PCR) process, and the point at the end of the baseline region represents an elbow or cycle threshold (Ct) value of the growth curve. In certain aspects, the regression process includes a Levenberg-Marquardt (LM) regression process. In certain aspects, a second maximum value is used as an initial condition for a second parameter, and the code further includes instructions to output the second parameter.

According to yet another aspect of the present invention, a kinetic Polymerase Chain Reaction (PCR) system is provided. The system typically includes a kinetic PCR analysis module that generates a PCR dataset representing a kinetic PCR amplification curve. The dataset typically includes a plurality of data points, each having a pair of coordinate values, wherein the dataset includes data points in a region of interest which includes a cycle threshold (Ct) value. The system also typically includes an intelligence module adapted to process the PCR dataset to determine the Ct value, by numerically determining second derivative values for data points along the PCR curve, determining a maximum value of the determined second derivative values, and calculating an approximation of a curve that fits the determined second derivative values by applying a regression process to a Gaussian Mixture Model function to determine one or more parameters of the function, wherein the parameters include initial conditions, and wherein the maximum value is used as an initial condition for a first parameter. The intelligence module is also typically adapted to output the first parameter, wherein the determined first parameter represents the Ct value. In certain aspects, the kinetic PCR analysis module is resident in a kinetic thermocycler device, and the intelligence module includes a processor communicably coupled to the analysis module. In certain aspects, the intelligence module includes a processor resident in a computer system coupled to the analysis module by one of a network connection or a direct connection. In certain aspects, the regression process includes a Levenberg-Marquardt (LM) regression process. In certain aspects, the system further includes a display module, such as a monitor, printer or other device capable of displaying textual and/or graphical data, wherein outputting includes displaying the Ct value on the display module.

According to yet another aspect of the present invention, a kinetic Polymerase Chain Reaction (PCR) system is provided. The system typically includes a kinetic PCR analysis module that generates a PCR dataset representing a kinetic PCR amplification curve. The dataset typically includes a plurality of data points, each having a pair of coordinate values, wherein the dataset includes data points in a region of interest which includes a cycle threshold (Ct) value. The system also typically includes an intelligence module adapted to process the PCR dataset to determine the Ct value, by numerically determining curvature values for data points along the PCR curve, determining a maximum value of the determined curvature values, and calculating an approximation of a curve that fits the determined curvature values by applying a regression process to a Gaussian Mixture Model function to determine one or more parameters of the function, wherein the parameters include initial conditions, and wherein the maximum value is used as an initial condition for a first parameter. The intelligence module is also typically adapted to output the first parameter, wherein the determined first parameter represents the Ct value. In certain aspects, the kinetic PCR analysis module is resident in a kinetic thermocycler device, and the intelligence module includes a processor communicably coupled to the analysis module. In certain aspects, the intelligence module includes a processor resident in a computer system coupled to the analysis module by one of a network connection or a direct connection. In certain aspects, the regression process includes a Levenberg-Marquardt (LM) regression process. In certain aspects, the system further includes a display module, such as a monitor, printer or other device capable of displaying textual and/or graphical data, wherein outputting includes displaying the Ct value on the display module.

Reference to the remaining portions of the specification, including the drawings and claims, will realize other features and advantages of the present invention. Further features and advantages of the present invention, as well as the structure and operation of various embodiments of the present invention, are described in detail below with respect to the accompanying drawings. In the drawings, like reference numbers indicate identical or functionally similar elements.

BRIEF DESCRIPTION OF THE DRAWINGS

FIG. 1 illustrates an example of a typical PCR growth curve, plotted as fluorescence intensity vs. cycle number.

FIG. 2 shows the second derivative of the Real-Time PCR curve in FIG. 1.

FIG. 3 shows the curvature of the Real-Time PCR curve in FIG. 1.

FIG. 5 illustrates an example of a Real-Time PCR curve with multiple Ct values.

FIG. 6 shows the second derivative of the Real-Time PCR curve in FIG. 5.

FIG. 7 shows the curvature of the Real-Time PCR curve in FIG. 5.

DETAILED DESCRIPTION

Figure 4:
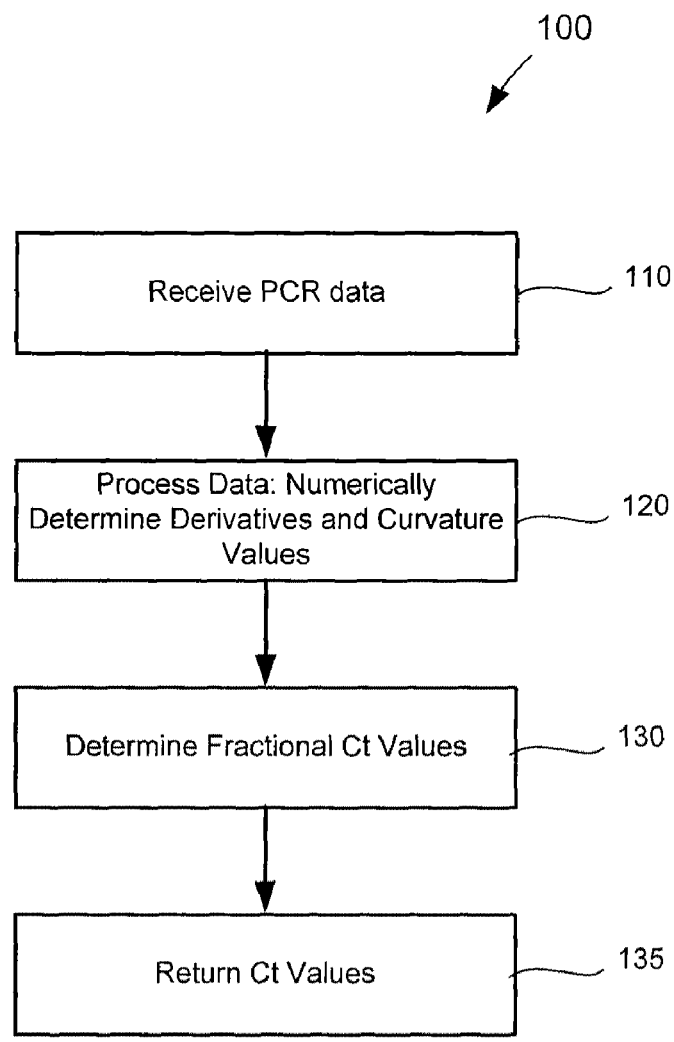
FIG. 4 illustrates a process for determining a transitionary value in a sigmoid curve, such as the elbow value or Ct value of a kinetic PCR amplification curve, according to one embodiment.

The present invention provides systems and methods for determining a transition value in a sigmoid or growth curve, such as the end of the baseline region or the elbow value or Ct value of a PCR amplification curve. In certain aspects, numerical determinations of the second derivatives and curvature values of a PCR data set are made. A Gaussian Mixture Model (GMM) function with parameters determined using a Levenberg-Marquardt (LM) regression process is used to find an approximation to the second derivative and the curvature curves. The maximum values of the numerically determined second derivative values and/or curvature values are used as initial conditions for parameters of the GMM function. The determined parameters provide fractional Ct values. The Ct value(s) are then returned and may be displayed or otherwise used for further processing.

One example of a growth or amplification curve 10 in the context of a PCR process is shown in FIG. 1. As shown, the curve 10 includes a lag phase region 15, and an exponential phase region 25. Lag phase region 15 is commonly referred to as the baseline or baseline region. Such a curve 10 includes a transitionary region of interest 20 linking the lag phase and the exponential phase regions. Region 20 is commonly referred to as the elbow or elbow region. The elbow region typically defines an end to the baseline and a transition in the growth or amplification rate of the underlying process. Identifying a specific transition point in region 20 can be useful for analyzing the behavior of the underlying process. In a typical PCR curve, identifying a transition point referred to as the elbow value or cycle threshold (Ct) value is useful for understanding qualitative and quantitative characteristics of the PCR process. For example, the Ct value can be used to provide quantization of the amount of DNA present in the sample being analyzed. Quantization is obtained by performing a calibration curve of the Log(DNA Amount) vs. Ct value. Subsequent samples can then use Ct values along with the calibration curve to directly obtain estimates of DNA in a sample. Ct values can also be used to provide qualitative information on the DNA sample.

Other processes that may provide similar sigmoid or growth curves include bacterial processes, enzymatic processes and binding processes. In bacterial growth curves, for example, the transition point of interest has been referred to as the time in lag phase, $\lambda$. Other specific processes that produce data curves that may be analyzed according to the present invention include strand displacement amplification (SDA) processes, nucleic acid sequence-based amplification (NASBA) processes and transcription mediated amplification (TMA) processes. Examples of SDA and NASBA processes and data curves can be found in Wang, Sha-Sha, et al., "Homogeneous Real-Time Detection of Single-Nucleotide Polymorphisms by Strand Displacement Amplification on the BD ProbeTec ET System," Clin Chem 2003 49(10):1599, and Weusten, Jos J. A. M., et al., "Principles of Quantitation of Viral Loads Using Nucleic Acid Sequence-Based Amplification in Combination With Homogeneous Detection Using Molecular Beacons," Nucleic Acids Research, 2002 30(6): 26, respectively, both of which are hereby incorporated by reference. Thus, although the remainder of this document will discuss embodiments and aspects of the invention in terms of its applicability to PCR curves, it should be appreciated that the present invention may be applied to data curves related to other processes.

As shown in FIG. 1, data for a typical PCR growth curve can be represented in a two-dimensional coordinate system, for example, with PCR cycle number defining the x-axis and an indicator of accumulated polynucleotide growth defining the y-axis. Typically, the indicator of accumulated growth is a fluorescence intensity value as the use of fluorescent markers is perhaps the most widely used labeling scheme. However, it should be understood that other indicators may be used depending on the particular labeling and/or detection scheme used. Examples of other useful indicators of accumulated signal growth include luminescence intensity, chemiluminescence intensity, bioluminescence intensity, phosphorescence intensity, charge transfer, voltage, current, power, energy, temperature, viscosity, light scatter, radioactive intensity, reflectivity, transmittance and absorbance. The definition of cycle can also include time, process cycles, unit operation cycles and reproductive cycles.

General Process Overview

Consider a typical Real-Time PCR growth curve as shown in FIG. 1. It is desired to obtain from FIG. 1 a number called the Ct or elbow value.

According to one embodiment, a process 100 for determining a transitionary value in a siginoid curve, such as the elbow value or Ct value of a kinetic PCR amplification curve, can be described briefly with reference to FIG. 4. In step 110, an experimental data set representing the curve is received or otherwise acquired. An example of a plotted PCR data set is shown in FIG. 1, where the y-axis and x-axis represent fluorescence intensity and cycle number, respectively, for a PCR curve. In certain aspects, the data set should include data that is continuous and equally spaced along an axis.

In the case where process 100 is implemented in an intelligence module (e.g., processor executing instructions) resident in a PCR data acquiring device such as a thermocycler, the data set may be provided to the intelligence module in real time as the data is being collected, or it may be stored in a memory unit or buffer and provided to the intelligence module after the experiment has been completed. Similarly, the data set may be provided to a separate system such as a desktop computer system or other computer system, via a network connection (e.g., LAN, VPN, intranet, Internet, etc.) or direct connection (e.g., USB or other direct wired or wireless connection) to the acquiring device, or provided on a portable medium such as a CD, DVD, floppy disk or the like. In certain aspects, the data set includes data points having a pair of coordinate values (or a 2-dimensional vector). For PCR data, the pair of coordinate values typically represents the cycle number and the fluorescence intensity value. After the data set has been received or acquired in step 110, the data set may be analyzed to determine the end of the baseline region.

In step 120, the data is numerically processed to determine derivative values and curvature values. The Ct or "elbow value" for these curves is obtained by finding the (fractional) cycle number (x-axis) corresponding to the maximum of the second derivative (y-axis) or the maximum of the curvature (y-axis). Using the data shown in FIG. 1, corresponding graphs for the second derivative and curvature are shown in FIG. 2 and FIG. 3.

In one embodiment, derivatives are obtained by use of the Savitzky-Golay (SG) method. [See A. Savitzky and Marcel J. E. Golay (1964). Smoothing and Differentiation of Data by Simplified Least Squares Procedures. Analytical Chemistry, 36: 1627-1639 and Press, W. H., et al. "Numerical Recipes in C, 2nd Ed.," Savitzky-Golay Smoothing Filters, Section 14.8, 650-655.] A SG-4-4-2 configuration (meaning 4 points to the left, 4 points to the right, and 2nd degree polynomial) is used to calculate the first and second derivative. The curvature is obtained by the formula shown in Equation 1 below. In this formula, x represents the cycle number, y represents the fluorescence value, and kappa ($\kappa$) represents the curvature.

$$\kappa = \frac{\frac{d^2 y}{dx^2}}{\left(1+\left(\frac{dy}{dx}\right)^2\right)^{3/2}} \quad (1)$$

Scale Invariant Forms of Curvature [Relative Curvature]

In certain embodiments, alternative methods are used to calculate curvature in order to allow the result to be scale-invariant. Scale invariant means that if fluorescence values are multiplied by a constant, the resulting Ct value is unchanged.

According to one method, the fluorescence value is divided by the mean fluorescence value before calculation of the curvature shown in equation (1). Thus, instead of y in equation (1), y is replaced by $y/y_{mean}$, where $$y_{mean} = \frac{1}{n}\sum_{i=1}^{n} y_i.$$

According to another method, the fluorescence value is divided by the growth of the PCR curve from baseline to plateau or the (maximum fluorescence−minimum fluorescence) before calculation of the curvature shown in equation (1). Thus, instead of y in equation (1), y is now replaced by y/AFI, where AFI=median(last five points)−median (first five points), or by y/growth, where growth=(maximum fluorescence−minimum fluorescence).

Dimensionless Forms of Second Derivative [Relative Second Derivative]

In addition to directly determining the second derivative, $$\frac{d^2 y}{dx^2},$$

a dimensionless (in y) form of the second derivative may be used by finding the maxima of the function:

$$\frac{1}{y}\frac{d^2 y}{dx^2}.$$

The equation-less method, however, is most advantageous when the real-time PCR data does not have a typical double sigmoid shape. Such a Real-Time PCR curve is shown in FIG. 5. A curve with this shape is not easily described any an analytical expression. This particular curve has multiple inflection points and multiple Ct values.

The second derivative and curvature plots corresponding to FIG. 5 is shown in FIG. 6 and FIG. 7. As before, the Ct values are obtained by determination of the cycle number corresponding to the maximum values of the second derivative and the curvature as shown in these two Figures. Two Ct values will be produced for the curve shown in FIG. 5.

Returning to FIG. 4, in one embodiment, fractional Ct values are determined in step 130. In order to find the maximum values of the curves, for example as shown in FIGS. 2 and 3 and FIGS. 6 and 7, in one embodiment, a Gaussian Mixture Model is fit to the data. The mean of the Gaussian Mixture Model corresponds to the maximum, and hence the Ct value. In one embodiment, a curve fit is done by calculating an approximation of a curve that fits the determined second derivative values and/or fits the determined curvature values by applying a regression process to a Gaussian Mixture Model function to determine one or more parameters of the function. In certain aspects, a Levenberg-Marquardt regression process is used. In one embodiment, for the case of a single peak, a Gaussian Mixture Model for one peak is used as shown in equation (2). If two peaks are present, a Gaussian Mixture Model for two peaks is used as shown in equation (3). The regressed values for the coefficients $\mu_1$ or ($\mu_1, \mu_2$) correspond to the Ct values for one and two peaks respectively. Gaussian Mixture Models are used in one embodiment, rather than taking additional derivatives to find the maximum, as higher order derivatives ($3^{rd}$, and $4^{th}$) can become unstable.

$$GMM_1 = \text{Exp}(-a_1) \cdot \text{Exp}\left(-\frac{1}{2}\left(\frac{x-\mu_1}{\sigma_1}\right)^2\right) \quad (2)$$

$$GMM_2 = \quad (3)$$
$$\text{Exp}(-a_1) \cdot \text{Exp}\left(-\frac{1}{2}\left(\frac{x-\mu_1}{\sigma_1}\right)^2\right) + \text{Exp}(-a_2) \cdot \text{Exp}\left(-\frac{1}{2}\left(\frac{x-\mu_2}{\sigma_2}\right)^2\right)$$

It should be appreciated that other models/functions could be used instead of a Gaussian Mixture Model as would be apparent to one skilled in the art. Examples of other models include Beta, Binomial, Cauchy, Chi, ChiSquare, Exponential, Extreme Value, FRatio, Gamma, Gumbel, Laplace, Logistic, Maxwell, Pareto, Rayleigh, StudentT, and Weibull models In one embodiment, the Levenberg-Marquardt (LM) method is used to curve fit equation (2) or equation (3). Details of this method can be found in the reference [Moré, J. J., "The Levenberg-Marquardt Algorithm, Implementation and Theory," *Numerical Analysis*, ed. Watson, G. A. Lecture Notes in Mathematics 630, Springer-Verlag, 1977, incorporated by reference herein]. It should be appreciated that other regression methods as are well known may be used. In general, the LM regression method includes an algorithm that requires various inputs and provides output. In one aspect, the inputs include a data set to be processed, a function (e.g., Gaussian Mixture Model) that is used to fit the data, and an initial guess for the parameters or variables of the function. The output includes a set of one or more parameters for the function that minimizes the distance between the function and the data set. It should be appreciated that other regression processes as would be apparent to one skilled in the art may be used.

One feature of the Levenberg-Marquardt method is that it requires good estimates of the parameter values prior to performing the regression. For the parameters $\alpha_1$ (or $\alpha_1, \alpha_2$), and $\sigma_1$ (or $\sigma_1, \sigma_2$) the initial conditions can be set equal to a constant (e.g., 1 or 2) in all cases. These parameters are generally not sensitive and will generally converge regardless of the initial conditions used. The parameters $\mu_1$ (or $\mu_1, \mu_2$) require more accurate initial conditions that should be determined for each curve. In one embodiment, a windowing method is used to calculate initial conditions for the parameters $\mu_1$ (or $\mu_1, \mu_2$) as described in more detail below.

In step 135, the Ct value(s) are returned, e.g., for display or further processing. Graphical displays may be rendered with a display device, such as a monitor screen or printer, coupled with the system that performed the analysis of FIG. 4, or data may be provided to a separate system for rendering on a display device.

In some embodiments, the $R^2$ statistic and/or confidence (e.g., 95% confidence) intervals are calculated for the $GMM_1$ and $GMM_2$ parameters. These values assess the quality of the curve fit and may be used in an Expert System (described below) to help determine whether the calculated Ct values are valid, invalid, or zero (no sample present). These values may also be displayed in step 135.

Determination of Maximum in Curves

In one embodiment, a windowing process is used on the data set to determine initial conditions for the parameters $\mu_1$, $\mu_2$. For finding the maximum of the curvature or the second derivatives all negative values are replaced by zero. In one embodiment, the windowing process searches for potential local maxima by using the following procedure:

1. Starting at the first point, examine the first several (e.g., five) points (points 1-5) of the data set.
2. If the middle y-Point is not the maximum in these five points, then there is no potential maximum in these five points. If the middle y-point is the maximum of these five points and it has a value greater than 0 (to avoid adding the middle points of a longer sequence of points with an exact value of 0 into the set of potential maxima), then there is a potential maximum. Add this point to the set of potential maxima S.
3. Advance the sliding window by one point (e.g., now points 2-6), and repeat the process described in item 2, again accepting only maximums at index 3 of these five points. Continue this process throughout the entire data set.
4. If the y-value of the penultimate point is higher or equal, the y-values of the previous two points and the ultimate point, add this point to the set of potential maxima S.
5. Examine the result set S of possible maximums, representing the set of possible maximums at index 3, and find the maximum data point in this set S of possible maximums (Smax).
6. If Smax is equal or less than a MaxNoise Input Parameter (a noise parameter that may be input by a user, or automatically determined), there is no peak in the curvature data.
7. Keep the remaining possible maximum data points from this set S, providing that they are greater than Smax×a RelativeMin Input Parameter and greater than an AbsoluteMin Input Parameter.
8. If there is only one data point left, there is only one peak, and the curve has only one maximum. Define this single peak as $pk_1$. If there are two data points left, then this represents a curve with two maximums. If there are more than two peaks, take the two peaks with the highest values of the data set S and return the peak with the lower cycle number of these two as $pk_1$ and the peak with the higher cycle number as $pk_2$.
9. The initial condition for $\mu_1$ is then $pk_1$ and the initial condition for $(\mu_1, \mu_2)$ is $(pk_1, pk_2)$.

Decline Detection

Figure 8:
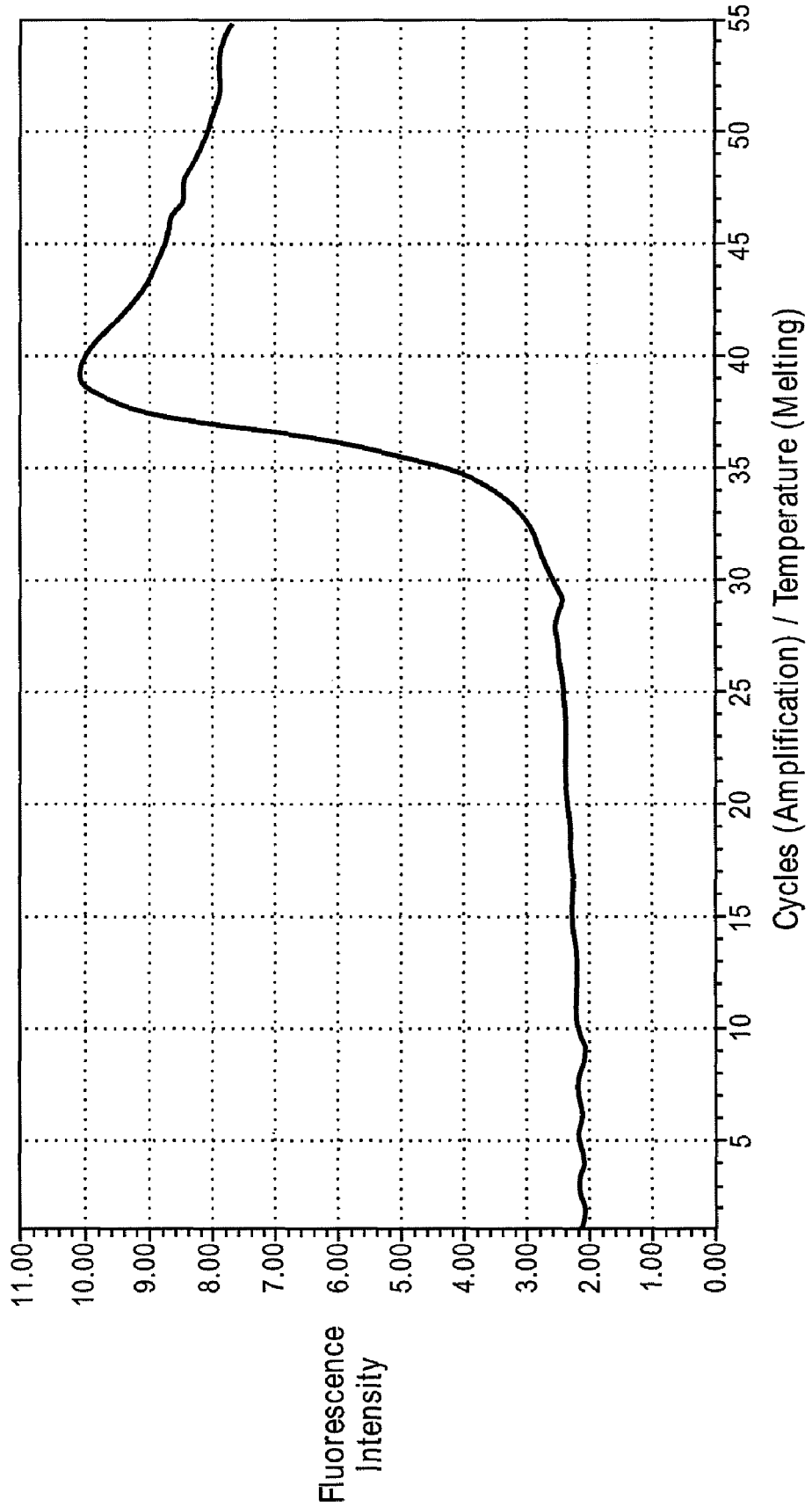
FIG. 8 illustrates an example of a decline in the fluorescence of the plateau region of a PCR data curve.
Figure 9:
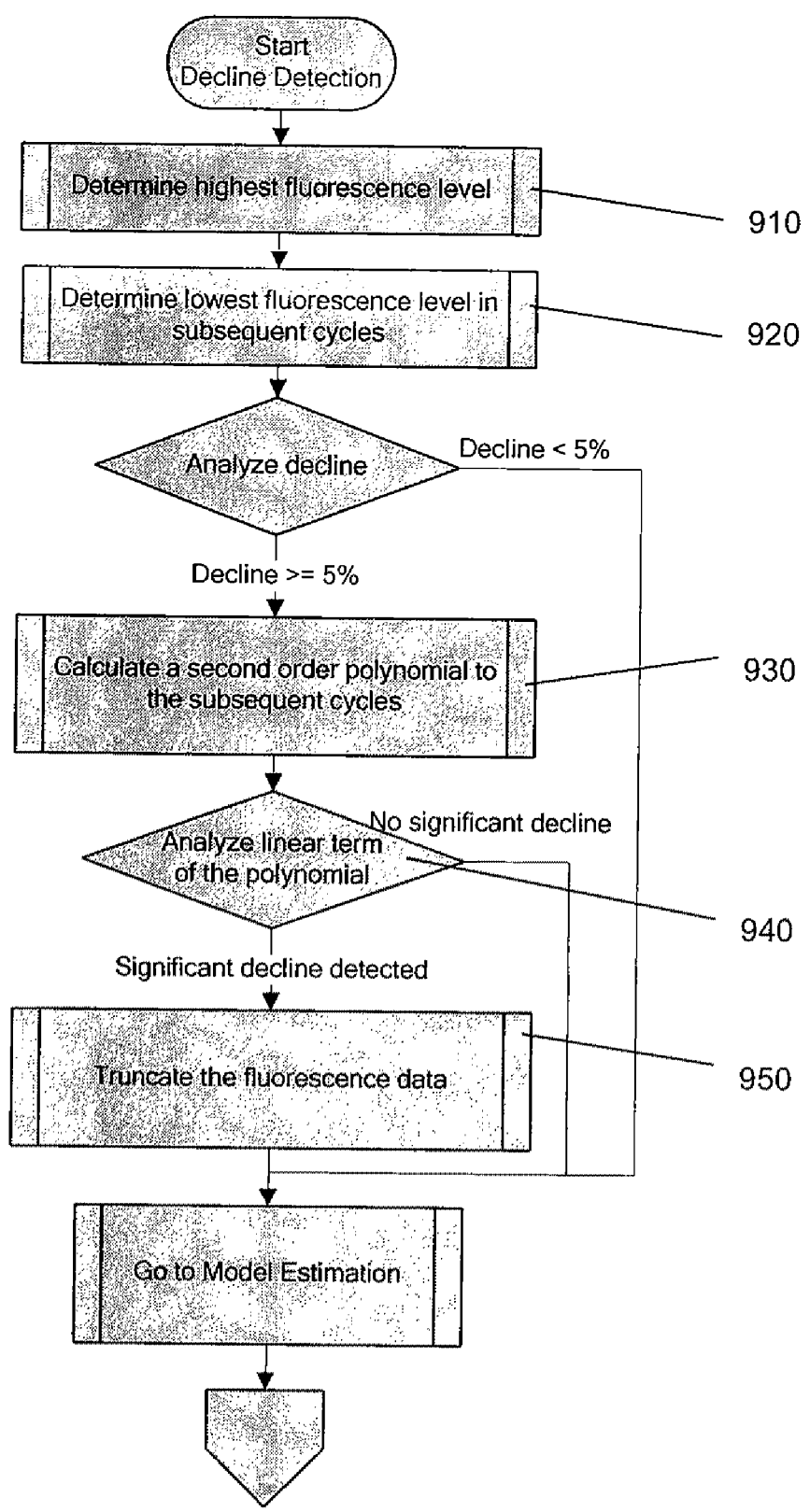
FIG. 9 illustrates a decline detection workflow according to one embodiment.

In some data, a decline in the intensity in a plateau region may exist. In such cases it is often desirable to account for this so as to remove undesirable effects. For example, a decline in the fluorescence of the plateau region can be seen in FIG. 8. The presence of such a plateau can cause a $C_T$ shift. In order to improve accuracy, in one embodiment, an automatic method for removing the declining segment of the fluorescence intensity data is implemented. Removal of a declining plateau is done prior to calculation of the second derivative or curvature in certain aspects. A decline detection workflow according to one embodiment is shown in FIG. 9.

In step 910 the cycle number corresponding to the highest fluorescence intensity is determined. In step 920 the fluorescence intensity at subsequent cycles (after the highest value) is evaluated if the highest fluorescence intensity was not in the last three cycles. If the highest fluorescence intensity is in the last three cycles, decline correction is not done. If the lowest fluorescence intensity in cycles after the cycle corresponding to the maximum fluorescence is less than 95% of the maximum fluorescence intensity, then a second order polynomial is fit to the fluorescence contained in the subsequent cycles (after the highest value) in step 930. In step 940, a determination is made as to whether there is significant decline in the data. In one embodiment, if the point of highest fluorescence intensity is greater than the value of an input parameter RV (relative value), the linear term of the second order polynomial is compared with the ratio of the maximum of the fluorescence intensities divided the number of data points, multiplied with a constant threshold value (e.g., −5). If the linear term is less than this number, indicating significant decline, then the fluorescence data that correspond to cycles after the cycle number with the highest fluorescence intensity are truncated in step 950; else no decline is present in the data and no action is necessary.

According to one embodiment, a second order polynomial fit is used for determination of a decline. In certain aspects, the fit can be performed using equation (4):

$$\begin{bmatrix} \sum_{i=k}^{m-1} x_i^4 & \sum_{i=k}^{m-1} x_i^3 & \sum_{i=k}^{m-1} x_i^2 \\ \sum_{i=k}^{m-1} x_i^3 & \sum_{i=k}^{m-1} x_i^2 & \sum_{i=k}^{m-1} x_i \\ \sum_{i=k}^{m-1} x_i^2 & \sum_{i=k}^{m-1} x_i & m-k \end{bmatrix} \begin{bmatrix} p \\ q \\ r \end{bmatrix} = \begin{bmatrix} \sum_{i=k}^{m-1} (x_i^2 \cdot y_i) \\ \sum_{i=k}^{m-1} (x_i \cdot y_i) \\ \sum_{i=k}^{m-1} y_i \end{bmatrix} \quad (4)$$

In equation (4), k is the cycle number corresponding to the maximum fluorescence intensity. Hence, if the value of q in equation (4) is less than the above mentioned product, then truncation of cycles after the cycle corresponding to the maximum fluorescence intensity is necessary for accurate nonlinear regression downstream. If a decline is detected and data truncation is done, then the fluorescence vector y, the cycle numbers vector x, and the length of the fluorescence vector m correspond to the truncated version and not the original inputs. The last three cycles are ignored because it is not possible to fit a quadratic function with less than three points.

Distinguishing Growth from Flat Line

Figure 10:
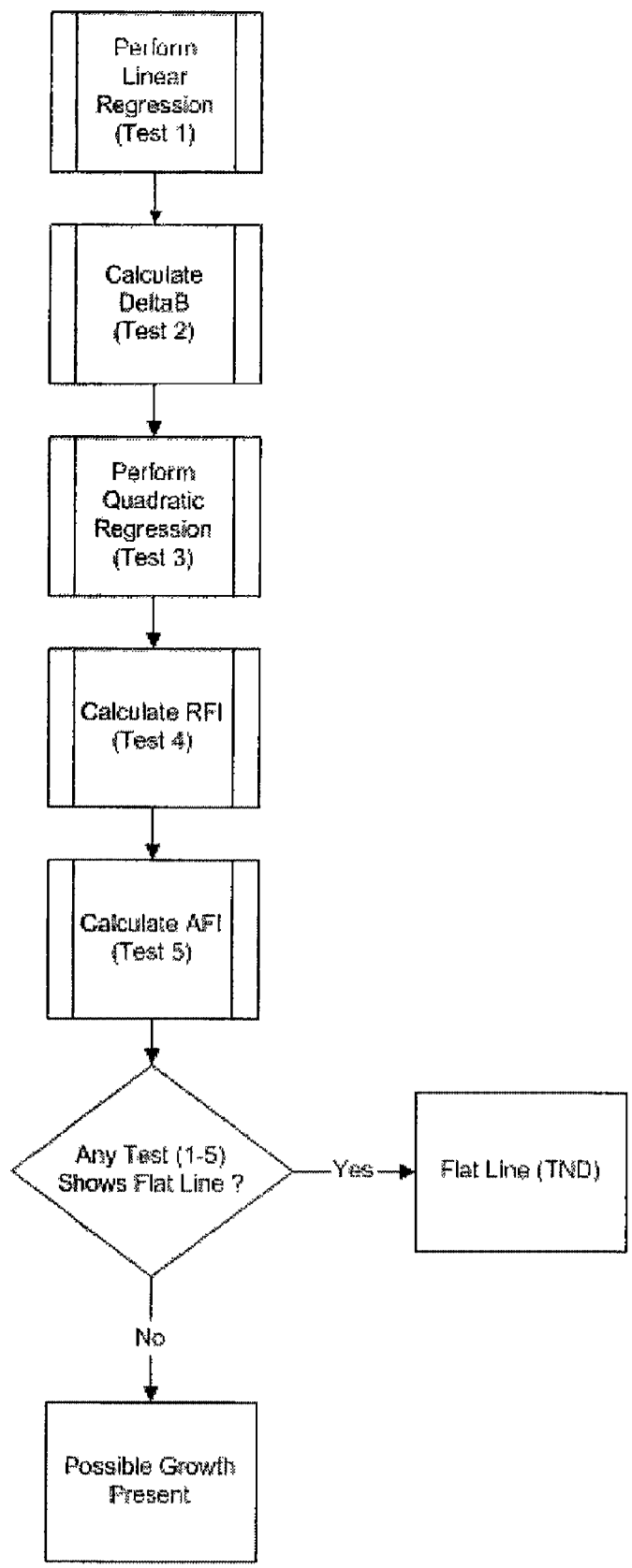
FIG. 10 illustrates five tests used to distinguish real growth of a curve from a flat line.

In some data, there may be insignificant growth. In such cases it is often desirable to account for this so as to remove undesirable effects. According to one embodiment, five tests are used to distinguish real growth of the curve from a flat line as shown in FIG. 10.

1. A linear regression fit is performed over either the entire or a portion of the RT-PCR curve. If $R^2$ for this linear regression >0.99, then it is assumed that there is no growth.
2. A statistic called DeltaB (shown below) is calculated. If 0<DeltaB<0.04, then it is assumed that there is no growth.

$$DeltaB = \begin{cases} \dfrac{\max_{i=5\ldots m-1} |linear(x_i) - y_i|}{\text{median}_{i=5\ldots m-1} |y_i|} & \text{if } m \geq 2 \text{ and } \text{median}_{i=5\ldots m-1} |y_i| > 0.001 \\ 0 & \text{otherwise} \end{cases}$$

3. A quadratic regression fit is performed over either the entire RT-PCR curve. If $R^2$ for this quadratic regression >0.98, then the RT-PCR curve is determined to have insufficient curvature for a growth curve.
4. A value called RFI (relative fluorescence increase) is calculated as:

$$RFI = \frac{\text{median[last 5 points]}}{\text{median[first 5 points]}}$$

In certain aspects, the RFI is calculated after the RT-PCR curve has been normalized by baseline subtraction. If the calculated RFI is less than an input $RFI_{min}$ value, then the curve is said to have no growth.

5. A value called AFI (relative fluorescence increase) is calculated as

AFI=median[last 5 points]−median[first 5 points]

In certain aspects, the AFI is calculated after the RT-PCR curve has been normalized by baseline subtraction. If the calculated AFI is less than an input $AFI_{min}$ value, then curve is said to have no growth.

It should be appreciated that one or more of the five tests described above may be used and/or other tests may be used to determine whether the curve can be considered to have growth. It should also be appreciated that different values may be used, for example, instead of using the first five points or last five points, more or less than 5 points may be used.

Algorithm Workflow

Figure 11:
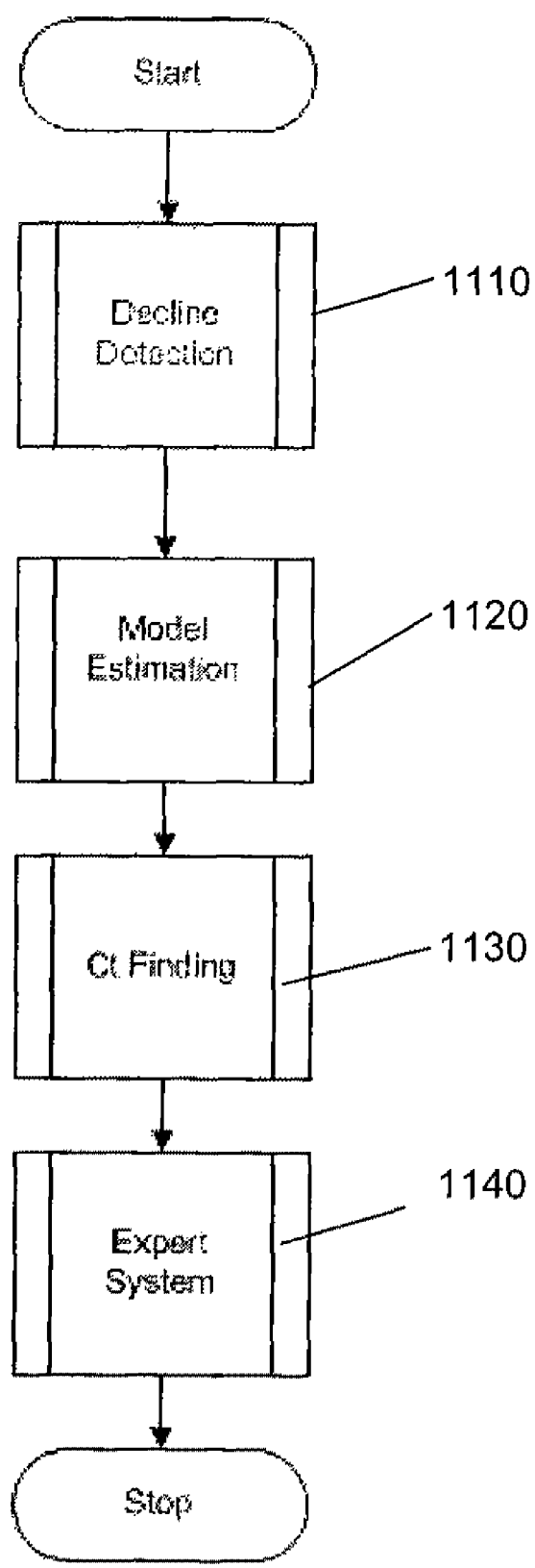
FIG. 11 illustrates a method of determining Ct values in growth curves according to one embodiment.
Figure 12:
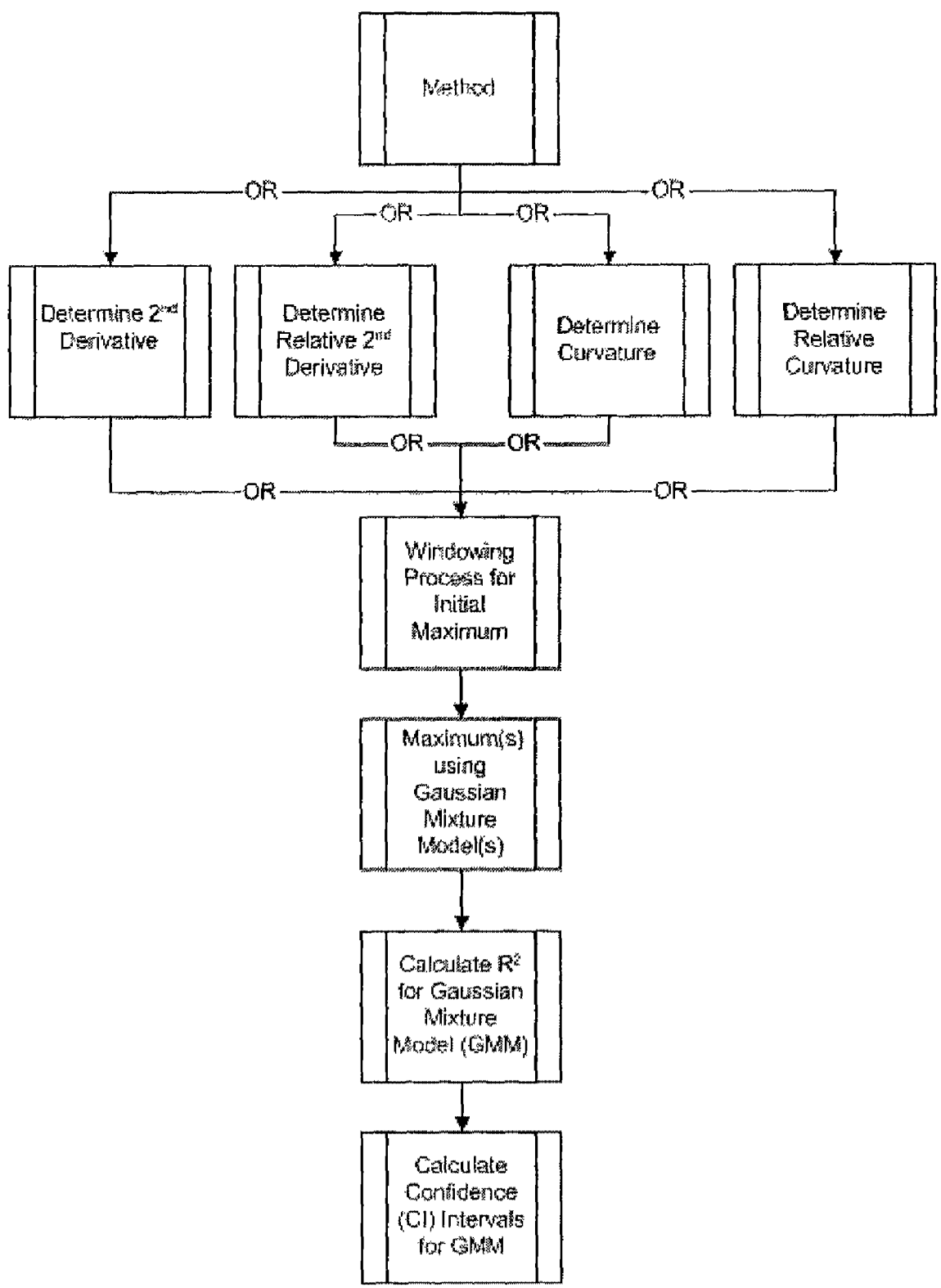
FIG. 12 illustrates the processing steps for a Ct finding routine according to one embodiment.

FIG. 11 illustrates a method of determining Ct values in growth curves according to one embodiment. In step 1110, decline detection is performed. In this step, a decline in fluorescence is determined and the fluorescence data is truncated if required. The procedure discussed above with reference to FIG. 9 is used in one embodiment. In step 1120, the data is first examined as to whether the data fits a straight line, or if there is possible growth present. If possible growth is present, than an Equation-Less Model is used, whereby the derivatives for the second derivative (or relative derivative) and curvature (or relative curvature) equations are calculated, for example, numerically using the Savitzky-Golay method. In step 1130, the CT value is determined. The Ct value is the fractional cycle number at which the second derivative (relative derivative) or curvature (relative curvature) of the PCR fluorescence model has its maximum. In one embodiment, the fractional cycle number is found by nonlinear regression of a one or two component Gaussian Mixture Model as described above with reference to FIG. 4, and equations (2) and (3). The processing steps for the Ct finding routine according to one embodiment are summarized in FIG. 12. In step 1140, an expert system processes the data to provide a suit of checks that are used for risk mitigation purposes.

Expert System Checks

Figure 13:
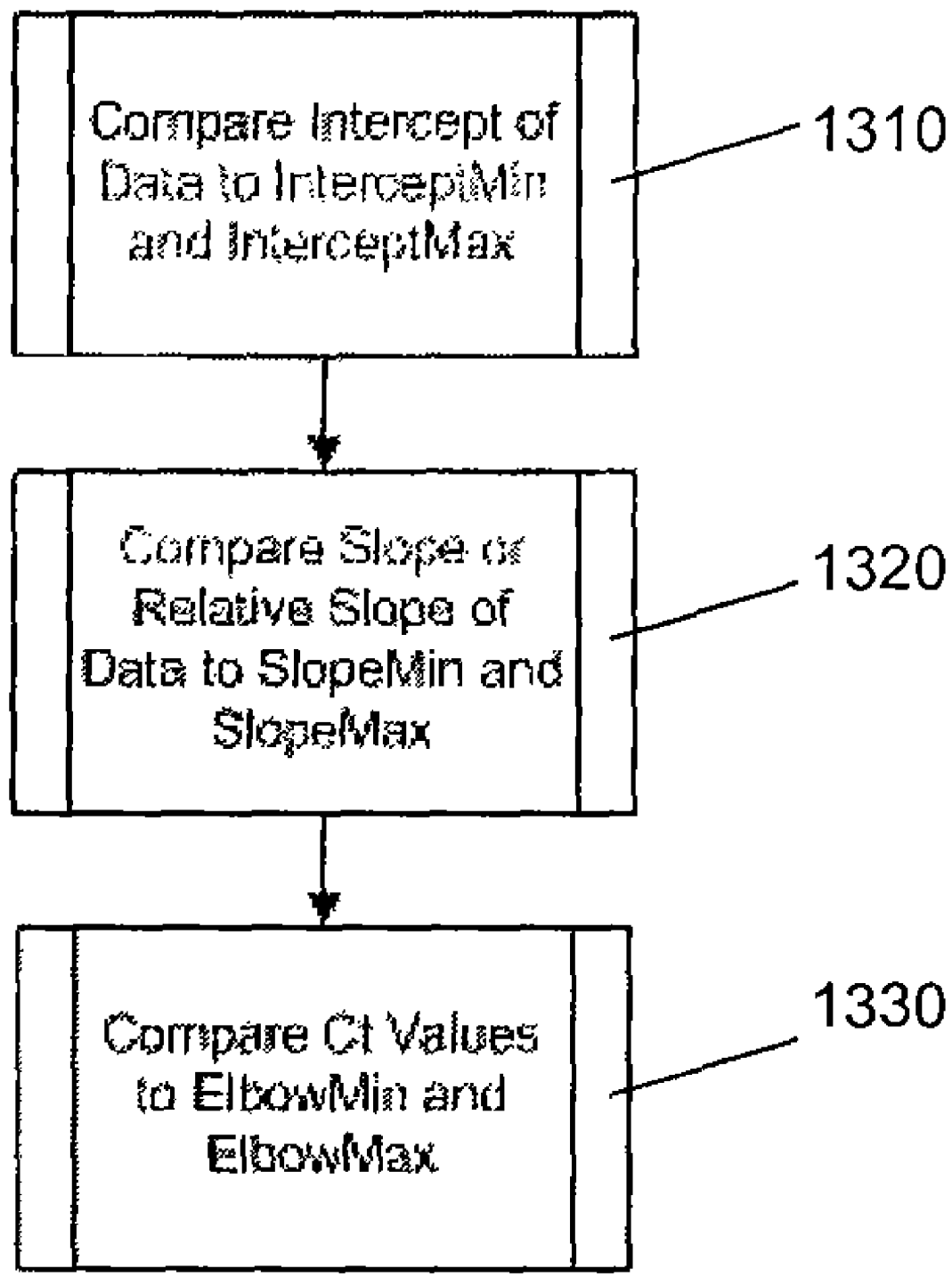
FIG. 13 illustrates expert system checks implemented in one embodiment.

In one embodiment, expert system checks are implemented as shown in FIG. 13. In step 1310, the system verifies whether the intercept of the PCR growth curve is within a user specified minimum and maximum value. If it is outside this range, then the curve is called invalid. In one aspect, the intercept is defined as the median of the first five points. In step 1320, the system verifies whether the slope of the PCR growth curve is within a user specified minimum and maximum value. If it is outside this range, then the curve is called invalid. Instead of slope, the relative slope may also be used, where the relative slope=slope/intercept. In this way, the slope comparison becomes scale invariant. In step 1330, the system verifies whether the Ct value(s) of the PCR growth curve is within a user specified minimum and maximum value. Flags are raised if either of these conditions are not satisfied. These curves may later be called invalid or negative.

EXAMPLE

Figure 14:
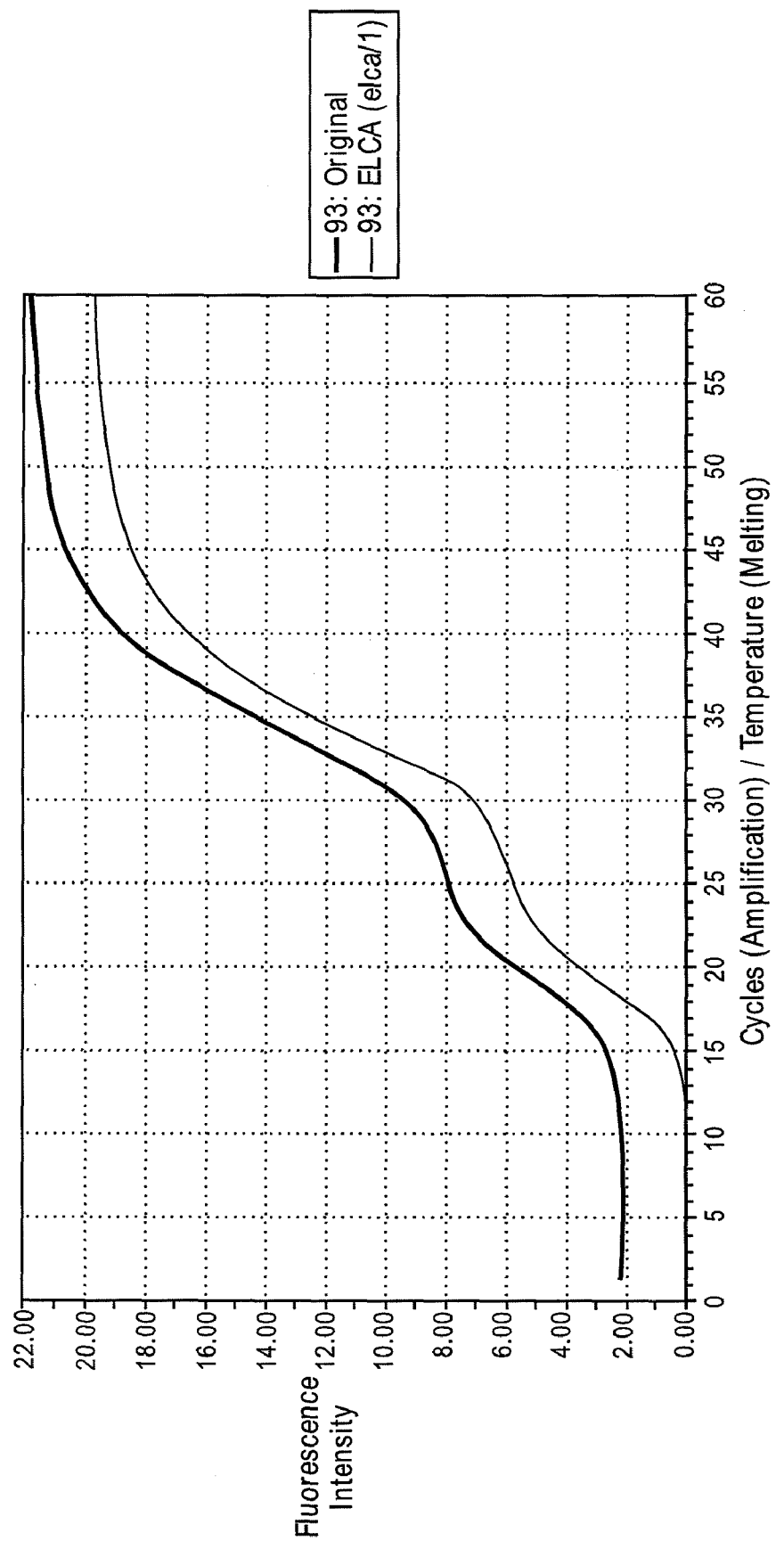
FIG. 14 shows an example of a typical real-time PCR curve with two elbows.

FIG. 14 shows a typical real-time PCR curve with two elbows. The top curve is the raw data, whereas the bottom curve is the curve after baseline subtraction. This data was analyzed with the algorithms second derivative, relative second derivative, curvature, and relative curvature. The results of the analysis are shown in Table 1 below. Two Ct values are given, corresponding to the two elbows present.

TABLE 1

Algorithm Results for Double Elbow Curves

| Method | 2nd Derivative | Relative 2$^{nd}$ Derivative | Curvature | Relative Curvature |
|---|---|---|---|---|
| Ct value (cycle) | (15.7, 30.0) | (15.2, 29.8) | (15.3, 29.4) | (13.7, 28.1) |

It should be appreciated that the Ct determination processes, including the derivative and curvature determination processes, may be implemented in computer code running on a processor of a computer system. The code includes instructions for controlling a processor to implement various aspects and steps of the Ct determination processes. The code is typically stored on a hard disk, RAM or portable medium such as a CD, DVD, etc. Similarly, the processes may be implemented in a PCR device such as a thermocycler including a processor executing instructions stored in a memory unit coupled to the processor. Code including such instructions may be downloaded to the PCR device memory unit over a network connection or direct connection to a code source or using a portable medium as is well known.

One skilled in the art should appreciate that the elbow determination processes of the present invention can be coded using a variety of programming languages such as C, C++, C#, Fortran, VisualBasic, etc., as well as applications such as Mathematica which provide pre-packaged routines, functions and procedures useful for data visualization and analysis. Another example of the latter is MATLAB®.

While the invention has been described by way of example and in terms of the specific embodiments, it is to be understood that the invention is not limited to the disclosed embodiments. To the contrary, it is intended to cover various modifications and similar arrangements as would be apparent to those skilled in the art. Therefore, the scope of the appended claims should be accorded the broadest interpretation so as to encompass all such modifications and similar arrangements.

What is claimed is:

1. A computer-implemented method of determining a point at the end of a baseline region of a growth curve, comprising the steps, implemented in a computer system having a processor, of:
   receiving a dataset representing a growth curve for a kinetic Polymerase Chain Reaction (PCR) process, said dataset including a plurality of data points each having a pair of coordinate values;
   numerically determining second derivative values for data points along the growth curve;
   determining a maximum value of the determined second derivative values;
   calculating an approximation of a curve that fits the determined second derivative values by applying a regression process to a Gaussian Mixture Model function to determine one or more parameters of the function, wherein said parameters include initial conditions, and wherein the maximum value is used as an initial condition for a first parameter; and
   outputting the first parameter, wherein the first parameter represents the end of the baseline region of the growth curve, and wherein the point at the end of the baseline region represents an elbow or cycle threshold (Ct) value of the growth curve.

2. The method of claim 1, further including displaying a value of the first parameter.

3. The method of claim 1, wherein the regression process includes a Levenberg-Marquardt (LM) regression process.

4. The method of claim 1, wherein a second maximum value is used as an initial condition for a second parameter, and wherein the method further includes outputting the second parameter.

5. The method of claim 1, wherein the Gaussian Mixture Model includes an expression of the form:

$$GMM_1 = \text{Exp}(-a_1) \cdot \text{Exp}\left(-\frac{1}{2}\left(\frac{x-\mu_1}{\sigma_1}\right)^2\right),$$

wherein $\mu_1$ is the first parameter, and wherein $\alpha_1$ and $\sigma_1$ are additional parameters.

6. The method of claim 1, further including determining whether the curve exhibits real growth by calculating a DeltaB statistic, where $$DeltaB = \begin{cases} \dfrac{\max\limits_{i=5\ldots m-1} |\text{linear}(x_i) - y_i|}{\text{median}\limits_{i=5\ldots m-1}|y_i|} & \text{if } m \geq 2 \text{ and } \text{median}\limits_{i=5\ldots m-1}|y_i| > 0.001 \\ 0 & \text{otherwise.} \end{cases}$$

7. A computer-implemented method of determining a point at the end of a baseline region of a growth curve, comprising the steps, implemented in a computer system having a processor, of:
   receiving a dataset representing a growth curve for a kinetic Polymerase Chain Reaction (PCR) process, said dataset including a plurality of data points each having a pair of coordinate values;
   numerically determining curvature values for data points along the growth curve;
   determining a maximum value of the determined curvature values;
   calculating an approximation of a curve that fits the determined curvature values by applying a regression process to a Gaussian Mixture Model function to determine one or more parameters of the function, wherein said parameters include initial conditions, and wherein the maximum value is used as an initial condition for a first parameter; and
   outputting the first parameter, wherein the first parameter represents the end of the baseline region of the growth curve, and wherein the point at the end of the baseline region represents an elbow or cycle threshold (Ct) value of the growth curve.

8. The method of claim 7, further including displaying a value of the first parameter.

9. The method of claim 7, wherein the regression process includes a Levenberg-Marquardt (LM) regression process.

10. The method of claim 7, wherein a second maximum value is used as an initial condition for a second parameter, and wherein the method further includes outputting the second parameter.

11. The method of claim 7, wherein the Gaussian Mixture Model includes an expression of the form:

$$GMM_1 = \text{Exp}(-a_1) \cdot \text{Exp}\left(-\frac{1}{2}\left(\frac{x-\mu_1}{\sigma_1}\right)^2\right),$$

wherein $\mu_1$ is the first parameter, and wherein $\alpha_1$ and $\sigma_1$ are additional parameters.

12. The method of claim 7, further including modifying the dataset so that the determined curvature values are scale invariant.

13. The method of claim 7, further including determining whether the curve exhibits real growth by calculating a DeltaB statistic, where $$DeltaB = \begin{cases} \dfrac{\max\limits_{i=5\ldots m-1} |linear(x_i) - y_i|}{\operatorname*{median}\limits_{i=5\ldots m-1}|y_i|} & \text{if } m \geq 2 \text{ and } \operatorname*{median}\limits_{i=5\ldots m-1}|y_i| > 0.001 \\ 0 & \text{otherwise.} \end{cases}$$

14. The method of claim 7, further including:
numerically determining second derivative values for data points along the growth curve;
determining a maximum value of the determined second derivative values;
calculating an approximation of a curve that fits the determined second derivative values by applying a regression process to a Gaussian Mixture Model function to determine one or more parameters of the function, wherein said parameters include initial conditions, and wherein the maximum value is used as an initial condition for a second parameter; and
outputting the second parameter, wherein the second parameter represents said end of the baseline region of the growth curve.

15. A non-transient computer readable medium that stores code for controlling a processor to determine a point at the end of the baseline region of a growth curve for a kinetic Polymerase Chain Reaction (PCR) process, the code including instructions which when executed by the processor cause the processor to:
receive a dataset representing a growth curve for a kinetic Polymerase Chain Reaction (PCR) process, said dataset including a plurality of data points each having a pair of coordinate values;
numerically determine second derivative values for data points along the growth curve;
determine a maximum value of the determined second derivative values;
calculate an approximation of a curve that fits the determined second derivative values by applying a regression process to a Gaussian Mixture Model function to determine one or more parameters of the function, wherein said parameters include initial conditions, and wherein the maximum value is used as an initial condition for a first parameter; and
output the first parameter, wherein the first parameter represents the end of the baseline region of the growth curve.

16. A non-transient computer readable medium that stores code for controlling a processor to determine a point at the end of the baseline region of a growth curve for a kinetic Polymerase Chain Reaction (PCR) process, the code including instructions which when executed by the processor cause the processor to:
receive a dataset representing a growth curve for a kinetic Polymerase Chain Reaction (PCR) process, said dataset including a plurality of data points each having a pair of coordinate values;
numerically determine curvature values for data points along the growth curve;
determine a maximum value of the determined curvature values;
calculate an approximation of a curve that fits the determined curvature values by applying a regression process to a Gaussian Mixture Model function to determine one or more parameters of the function, wherein said parameters include initial conditions, and wherein the maximum value is used as an initial condition for a first parameter; and
output the first parameter, wherein the first parameter represents the end of the baseline region of the growth curve.

17. A kinetic Polymerase Chain Reaction (PCR) system, comprising:
a kinetic PCR analysis device that generates a PCR dataset representing a kinetic PCR amplification curve, said dataset including a plurality of data points, each having a pair of coordinate values, wherein said dataset includes data points in a region of interest which includes a cycle threshold (Ct) value; and
a processor adapted to process the PCR dataset to determine the Ct value, by:
numerically determining second derivative values for data points along the PCR curve;
determining a maximum value of the determined second derivative values;
calculating an approximation of a curve that fits the determined second derivative values by applying a regression process to a Gaussian Mixture Model function to determine one or more parameters of the function, wherein said parameters include initial conditions, and wherein the maximum value is used as an initial condition for a first parameter; and
outputting the first parameter, wherein the first parameter represents the Ct value.

18. A kinetic Polymerase Chain Reaction (PCR) system, comprising:
a kinetic PCR analysis device that generates a PCR dataset representing a kinetic PCR amplification curve, said dataset including a plurality of data points, each having a pair of coordinate values, wherein said dataset includes data points in a region of interest which includes a cycle threshold (Ct) value; and
a processor adapted to process the PCR dataset to determine the Ct value, by:
numerically determining curvature values for data points along the PCR curve;
determining a maximum value of the determined curvature values;
calculating an approximation of a curve that fits the determined curvature values by applying a regression process to a Gaussian Mixture Model function to determine one or more parameters of the function, wherein said parameters include initial conditions, and wherein the maximum value is used as an initial condition for a first parameter; and
outputting the first parameter, wherein the first parameter represents the Ct value.

19. The PCR system of claim 17, wherein the kinetic PCR analysis device is resident in a kinetic thermocycler device, and wherein the processor is communicably coupled to the analysis device.

20. The PCR system of claim 18, wherein the kinetic PCR analysis device is resident in a kinetic thermocycler device, and wherein the processor is communicably coupled to the analysis device.

21. The PCR system of claim 17, wherein the processor is resident in a computer system coupled to the analysis device by one of a network connection or a direct connection.

22. The PCR system of claim 18, wherein the processor is resident in a computer system coupled to the analysis device by one of a network connection or a direct connection.

23. The PCR system of claim 17, further including a display module, wherein outputting includes displaying the Ct value on the display module.

24. The PCR system of claim 18, further including a display module, wherein outputting includes displaying the Ct value on, the display module.

25. The PCR system of claim 17, wherein a second maximum value is used as an initial condition for a second parameter, and wherein the method further includes outputting the second parameter.

26. The PCR system of claim 18, wherein a second maximum value is used as an initial condition for a second parameter, and wherein the method further includes outputting the second parameter.

27. The PCR system of claim 17, wherein, the Gaussian Mixture Model includes an expression of the form:

$$GMM_1 = \text{Exp}(-a_1) \cdot \text{Exp}\left(-\frac{1}{2}\left(\frac{x-\mu_1}{\sigma_1}\right)^2\right),$$

wherein $\mu_1$ is the first parameter, and wherein $\alpha_1$ and $\sigma_1$ are additional parameters.

28. The PCR system of claim 18, wherein the Gaussian Mixture Model includes an expression of the form:

$$GMM_1 = \text{Exp}(-a_1) \cdot \text{Exp}\left(-\frac{1}{2}\left(\frac{x-\mu_1}{\sigma_1}\right)^2\right),$$

wherein $\mu_1$ is the first parameter, and wherein $\alpha_1$ and $\sigma_1$ are additional parameters.

29. The PCR system of claim 17, wherein the processor is further adapted to process the PCR dataset to determine whether the curve exhibits real growth by calculating a DeltaB statistic, where $$DeltaB = \begin{cases} \dfrac{\max\limits_{i=0...m-1}|\text{linear}(x_i) - y_i|}{\text{median}\limits_{i=0...m-1}|y_i|} & \text{if } m \geq 2 \text{ and } \text{median}\limits_{i=0...m-1}|y_i| > 0.001 \\ 0 & \text{otherwise.} \end{cases}$$

30. The PCR system of claim 18, wherein the processor is further adapted to process the PCR dataset to determine whether the curve exhibits real growth by calculating a DeltaB statistic, where $$DeltaB = \begin{cases} \dfrac{\max\limits_{i=0...m-1}|\text{linear}(x_i) - y_i|}{\text{median}\limits_{i=0...m-1}|y_i|} & \text{if } m \geq 2 \text{ and } \text{median}\limits_{i=0...m-1}|y_i| > 0.001 \\ 0 & \text{otherwise.} \end{cases}$$

31. The PCR system of claim 17, wherein the regression process includes a Levenberg-Marquardt (LM) regression process.

32. The PCR system of claim 18, wherein the regression process includes a Levenberg-Marquardt (LM) regression process.

* * * * *